(12) United States Patent
Klaiman et al.

(10) Patent No.: US 9,005,139 B2
(45) Date of Patent: Apr. 14, 2015

(54) DEVICE, SYSTEM AND METHOD FOR SIZING OF TISSUE OPENINGS

(75) Inventors: Moshe Klaiman, Gedera (IL); Ran Carmeli, Moshav Rinatya (IL); Itai Yonat, Tel-Aviv (IL); Eyal Teichman, Hod-HaSharon (IL)

(73) Assignee: Assis Medical Ltd., Herzlia (IL)

( * ) Notice: Subject to any disclaimer, the term of this patent is extended or adjusted under 35 U.S.C. 154(b) by 121 days.

(21) Appl. No.: 13/139,305

(22) PCT Filed: Dec. 2, 2009

(86) PCT No.: PCT/IL2009/001134
§ 371 (c)(1),
(2), (4) Date: Jun. 13, 2011

(87) PCT Pub. No.: WO2010/070633
PCT Pub. Date: Jun. 24, 2010

(65) Prior Publication Data
US 2011/0245859 A1  Oct. 6, 2011

Related U.S. Application Data

(60) Provisional application No. 61/122,442, filed on Dec. 15, 2008.

(51) Int. Cl.
*A61B 5/00* (2006.01)
*A61B 5/02* (2006.01)
*A61B 5/107* (2006.01)
*A61F 2/24* (2006.01)

(52) U.S. Cl.
CPC ........... *A61B 5/1076* (2013.01); *A61B 5/02007* (2013.01); *A61B 5/6853* (2013.01); *A61B 2562/0247* (2013.01); *A61F 2/2496* (2013.01)

(58) Field of Classification Search
USPC .................................. 606/192; 600/547, 587
See application file for complete search history.

(56) References Cited

U.S. PATENT DOCUMENTS

| | | | |
|---|---|---|---|
| 5,035,246 A | 7/1991 | Heuvelmans et al. | |
| 5,868,708 A * | 2/1999 | Hart et al. | 604/104 |
| 6,695,809 B1 * | 2/2004 | Lee | 604/96.01 |
| 7,951,111 B2 * | 5/2011 | Drasler et al. | 604/103.13 |

(Continued)

FOREIGN PATENT DOCUMENTS

| | | |
|---|---|---|
| WO | WO 2007/076045 | 7/2007 |
| WO | WO 2010/070633 | 6/2010 |

OTHER PUBLICATIONS

International Preliminary Report on Patentability Dated Jun. 30, 2011 From the International Bureau of WIPO Re. Application No. PCT/IL2009/001134.

(Continued)

*Primary Examiner* — Max Hindenburg

(57) ABSTRACT

A device for determining a physical parameter of a tissue opening is provided. The device includes an expandable member which is designed for positioning within a tissue opening such as a valve annulus. The expandable member is capable of expanding while applying an inward radial force indicative of a diameter thereof. When the expandable member is positioned within the tissue opening and expanded, an increase in the inward radial force induced by contact between the expandable member and tissue surrounding the opening can be utilized to derive information relating to the physical parameter of the tissue opening.

10 Claims, 10 Drawing Sheets

(56) References Cited

U.S. PATENT DOCUMENTS

2001/0007956 A1* 7/2001 Letac et al. .................. 623/2.11
2005/0261722 A1* 11/2005 Crocker et al. ............... 606/192
2007/0010844 A1* 1/2007 Gong et al. .................. 606/192
2008/0009746 A1* 1/2008 Forster et al. ................ 600/467
2008/0275483 A1* 11/2008 Makower et al. ............ 606/192

OTHER PUBLICATIONS

International Search Report and the Written Opinion Dated Mar. 29, 2010 From the International Searching Authority Re.: Application No. PCT/IL2009/001134.

* cited by examiner

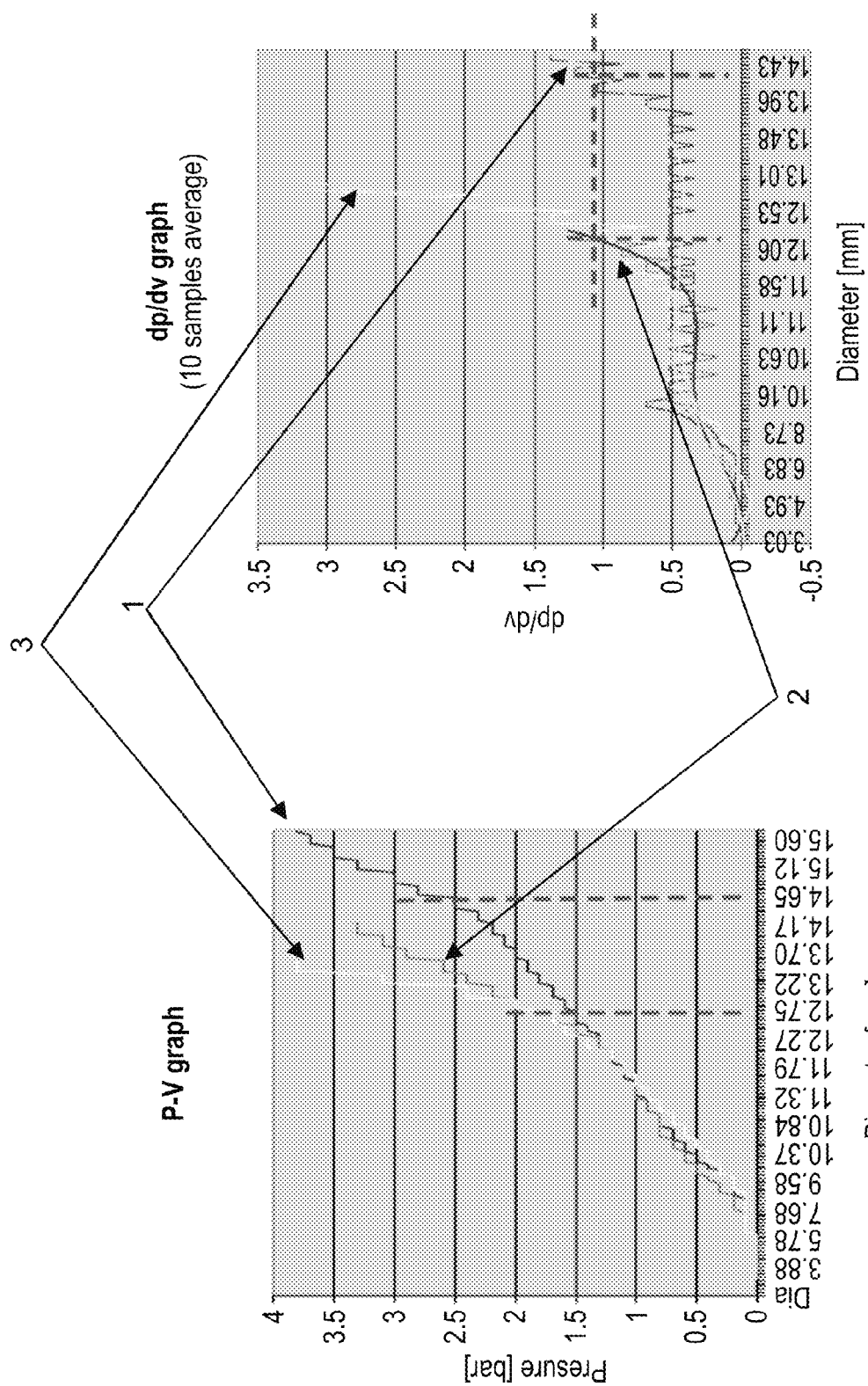

DEVICE, SYSTEM AND METHOD FOR SIZING OF TISSUE OPENINGS

RELATED APPLICATIONS

This application is a National Phase of PCT Patent Application No. PCT/IL2009/001134 having International filing date of Dec. 2, 2009, which claims the benefit of priority of U.S. Provisional Patent Application No. 61/122,442 filed on Dec. 15, 2008. The contents of the above applications are all incorporated herein by reference.

FIELD AND BACKGROUND OF THE INVENTION

The present invention relates to a system and method which can be used to provide a physician with information relating to a physical or functional parameter of a tissue opening such as a heart valve, and optionally prepare a valve for a subsequent valve replacement or repair procedure.

Heart valve abnormalities such as valvular insufficiency and valvular stenosis can result in insufficient opening or closure of a heart valve.

Valvular insufficiency is a common cardiac abnormality where the valve leaflets do not completely close. This allows regurgitation (i.e., backward leakage of blood at a heart valve). Such regurgitation requires the heart to pump both the regular volume of blood and the blood that has regurgitated. Such added workload can eventually result in heart failure.

Valvular stenosis or calcification is a calcium buildup in the valve which impedes proper valve leaflet movement and can severely limit opening of the valve.

Traditionally, heart valve abnormalities are treated via open heart surgery, however, in individuals whose heart function is too severely compromised to withstand surgery; percutaneous approaches for treating heart valve disease have been developed.

Percutaneous valvotomy (also called valvuloplasty) is typically performed to treat mitral valve and pulmonic valve stenosis; in some patients it may also be performed to treat stenosis of the aortic valve.

Although valvuloplasty is effective in treatment of mitral and pulmonic valve stenosis, it is not considered effective in treatment of severe symptomatic aortic stenosis; studies have shown that valve replacement is the only viable option for effective treatment. The need for a valve replacement solution combined with the need for minimally invasive surgery has led to the development of percutaneous valve replacement approaches.

Percutaneous valve replacement (PVR) is performed by placing a catheter through the femoral artery (in the groin) or through a radial artery and guiding it into the chambers of the heart. A compressed tissue heart valve is placed on the balloon-mounted catheter and is positioned directly over the diseased aortic valve. Once in position, the balloon is inflated to secure the valve in place.

At present, work on percutaneous valve replacement is proceeding at a pace that reflects intensifying professional and commercial interest. However, this approach is still in the clinical investigational stage and is yet to be accepted as a viable treatment option.

Although percutaneous valve replacement approaches are well known in the prior art, the present inventors believe that there remains a need for a percutaneous valve assessment system which can be used by a physician to determine at least one physical parameter of an abnormal valve and optionally prepare such an abnormal valve for a subsequent valve replacement procedure.

SUMMARY OF THE INVENTION

According to one aspect of the present invention there is provided a device for determining a physical parameter of a tissue opening comprising an expandable member designed for positioning within the tissue opening, the expandable member being capable of expanding while applying an inward radial force indicative of a diameter thereof, such that when the expandable member is positioned within the tissue opening and expanded, an increase in the inward radial force can be indicative of contact between the expandable member and tissue surrounding the tissue opening.

According to further features in preferred embodiments of the invention described below, the increase in the inward radial force can be utilized to derive information relating to the physical parameter of the tissue opening.

According to still further features in the described preferred embodiments the expandable member includes an inflatable balloon at least partially covered by a structure.

According to still further features in the described preferred embodiments the structure is a wire mesh, a wire spiral or wire struts.

According to still further features in the described preferred embodiments the structure is a tube.

According to still further features in the described preferred embodiments the inflatable balloon is a non-compliant balloon.

According to still further features in the described preferred embodiments the tissue opening is a valve annulus.

According to still further features in the described preferred embodiments the expandable member is designed for positioning within the valve annulus.

According to still further features in the described preferred embodiments the expandable member has an elastic diameter range of 4-35 mm.

According to still further features in the described preferred embodiments the physical parameter is a diameter of the tissue opening.

According to still further features in the described preferred embodiments the device further comprises a plurality of imaging markers attached to the expandable member.

According to still further features in the described preferred embodiments the plurality of imaging markers are arranged in a pattern selected for indicating a cross sectional shape of the expandable member when in an expanded state.

According to still further features in the described preferred embodiments the plurality of imaging markers are arranged in a pattern selected for indicating an imaging projection which is most perpendicular to the expandable member and thus most perpendicular to the organ.

According to another aspect of the present invention there is provided a device for determining a physical and/or functional parameter of a tissue opening comprising an expandable member designed for positioning within the tissue opening, the expandable member being capable of elastic expansion without substantial structural deformation when expanded beyond a tissue contact diameter within the tissue opening.

According to yet another aspect of the present invention there is provided a system for determining a physical and/or functional parameter of a tissue opening comprising the device of claim 1 or 13 and a delivery catheter for delivering the device to the tissue opening.

According to still further features in the described preferred embodiments the delivery catheter is configured for positing within a blood vessel.

According to still further features in the described preferred embodiments the delivery catheter is an over-the-wire catheter configuration.

According to still further features in the described preferred embodiments the system further comprises a mechanism for expanding the expandable member.

According to still further features in the described preferred embodiments the mechanism for expanding the expandable member is a fluid pump being in fluid communication with the expandable member.

According to still further features in the described preferred embodiments the system further comprises a mechanism for determining an expansion state of the expandable member.

According to still further features in the described preferred embodiments the mechanism for determining the expansion state of the expandable member includes at least one pressure sensor.

According to still further features in the described preferred embodiments the system further comprises a controller for controlling expansion of the device.

According to still further features in the described preferred embodiments the controller includes a user interface for providing information relating to an expansion state of the device.

According to still further features in the described preferred embodiments the device includes a non-compliant balloon at least partially covered by a compliant structure and the information is a volume of fluid in the non-compliant balloon.

According to still further features in the described preferred embodiments the device includes a non-compliant balloon at least partially covered by a compliant structure and the information is a pressure-volume relationship within the non-compliant balloon.

According to still further features in the described preferred embodiments the device includes a computer system for processing data (markers imaging) and outputting physical or functional parameters of the organ.

According to yet another aspect of the present invention there is provided a system for determining a physical and/or functional parameter of a tissue opening comprising: (a) a device including a semi-compliant balloon; and (b) a controller for introducing fluid into the semi-compliant balloon and for measuring a volume and/or pressure of the fluid introduced into the semi-compliant balloon.

According to still further features in the described preferred embodiments the semi-compliant balloon is constructed from a non-compliant balloon at least partially covered by a compliant cage structure or from a balloon having a compliant mid section flanked by non-compliant end portions.

According to still further features in the described preferred embodiments the system further comprises a user interface for providing a user with pressure and volume of the semi-compliant balloon and optionally dP/dV data.

According to yet another aspect of the present invention there is provided method of sizing a tissue opening comprising (a) inflating a semi-compliant inflatable structure within the tissue opening; (b) measuring volume and pressure of the inflatable structure during the inflation; and (c) utilizing the volume and pressure measurements to determine a point of contact between the inflatable structure and tissue of the tissue opening to thereby size the tissue opening.

According to still further features in the described preferred embodiments the tissue opening is a valve annulus.

According to still further features in the described preferred embodiments the semi-compliant inflatable structure is a non-compliant balloon at least partially covered by a compliant cage structure According to still further features in the described preferred embodiments the semi-compliant inflatable structure is a balloon having a compliant mid section flanked by non-compliant end portions.

The present invention successfully addresses the shortcomings of the presently known configurations by providing a device which can be used to determine a size and shape of a wide range of tissue opening sizes while also enabling preparation of a heart valve annulus for subsequent valve replacement.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3A-*collapsed* balloon and cage; FIG. 3B-fluid-filled balloon and expanded cage.

FIGS. 11A-B are graphs illustrating the pressure/volume (FIG. 11A-*identical* to FIG. 10) and dP/dV (FIG. 11B) measurements from the semi-complaint balloon of the present invention.

DESCRIPTION OF THE PREFERRED EMBODIMENTS

Figure 1A:
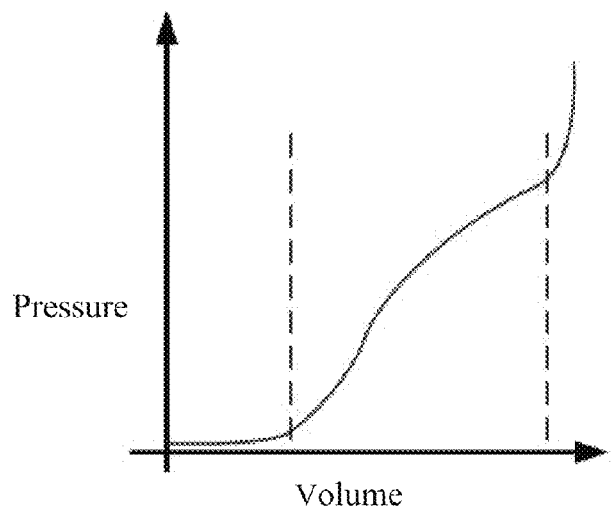
FIGS. 1A-C illustrate the pressure-volume response curve of the expandable member of the present device (FIG. 1A), a prior non-compliant balloon (FIG. 1B) and a prior art compliant balloon (FIG. 1C).

The present invention is of a device, system and method which can be used to accurately assess physical parameters of a tissue opening such as a vessel or an organ lumen or valve annulus.

Specifically the present invention can be used to determine a size and shape of any heart valve, as well as prepare defective heart valves for subsequent valve replacement therapy.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Assessment of size of a vessel lumen or a heart valve is crucial for successful treatment of disorders associated with such tissue structures. For example, effective percutaneous heart valve replacement relies upon accurate matching of a replacement valve with an annulus size of a defective heart valve.

A heart valve is composed of an annulus which supports three thin and pliable leaflets. In the case of an aortic valve, normal aortic valve leaflets spread apart easily and cause no obstruction to outflow of the blood from the heart. In valve replacement therapy, leaflet functionality is replaced by a prosthetic device which is anchored to annulus tissue and as such, correct sizing of the annulus is a prerequisite step in this procedure.

Devices suitable for assessing the size, shape, and topography of tissue lumens of vessels and valves and hollow portions of organs are known in the art.

Such devices typically employ an imaging probe (e.g. an ultrasound transducer) or an expandable member which is positionable within a lumen or valve annulus and includes an imaging-sensitive marker pattern or contrast medium.

For example, U.S. Pat Application No. 20080009746 describes an expandable structure (e.g. balloon) which is expanded such that it engages and applies pressure to the internal walls of the target location, such as the valve annulus. The expandable structure takes on the shape of the internal surface of the target location and is then imaged (via an internal or external imaging device) to derive size and shape information.

Although this device can be utilized to size a valve annulus or a vessel lumen, it is limited by complicated, time consuming and costly imaging approaches.

A sizing approach which traverses the need for imaging is described in WO publication No. 2008042347. This publication describes a balloon catheter which includes pressure and diameter sensors along with a feedback system to control the dilation of the balloon. The pressure information received from the sensors can be used to derive diameter and volume information. Although such a device can be utilized to size vessel lumens and detect narrowing regions therein, it cannot be effectively utilized for sizing an annulus of a valve since valve annulus sizes vary and thus accurate sizing of a valve annulus requires a device which can provide size information over a wide range of sizes.

While reducing the present invention to practice, the present inventors have devised an approach for sizing a tissue opening such as a valve annulus without having to employ several sizing devices each capable of sizing a specific annulus size or internal or external imaging. The present approach utilizes a device which is constructed having multi-sizing capabilities and is thus useful in sizing tissue structures, such as heart valves, which vary in shape and size from one individual to the next.

The present device employs an expandable member which is elastically expandable through a wide range of diameters (e.g. 4-35 mm) while providing predictable pressure feedback throughout this range. As is further described in the Examples section which follows, such predictable pressure feedback enables accurate assessment of annulus diameter and shape.

Although prior art catheter balloons (e.g. WO publication No. 2008042347) can also be used to correlate internal filling pressure with volume and diameter, such balloons suffer from several inherent limitations. In non-compliant balloons, build up of pressure can only be detected once the balloon reaches a fully expanded state and as such, the feedback range of such balloon is limited and as such they cannot be utilized for sizing of a wide range of annulus sizes.

In compliant balloons, the range of effective expansion does not cover typical annulus sizes, since the behavior of compliant balloons cannot be reliably predicted at both low and high pressures. For example, compliant balloons can be inflated to a point of bursting without noticeable feedback in as far as internal pressure changes.

In addition, both non-compliant balloons and compliant balloons will tend to inflate 'around' externally applied forces (the inflation medium will follow the path of least resistance) and as such, they will bulge around a valve annulus (forming a dumbbell shape) and will be ineffective at providing accurate pressure feedback at tissue contact. With additional inflation, such bulging can lead to balloon bursting in the case of compliant balloons or application of excessive force to a tissue surrounding an opening (e.g. valve annulus) in the case of non-compliant balloons.

To enable the above described functionality, the device of the present invention was constructed according to the following guidelines:

(i) Minimal diameter when collapsed—In its non-inflated shape, the present device assumes a diameter suitable for percutaneous delivery. An embodiment of the present device having a compliant cage constructed from a super elastic material would apply pressure to the non-compliant balloon (encapsulated by the cage) and compact it to a minimal diameter.

(ii) Control over the point of contact between the device and tissue of the annulus—during expansion of the device, the pressure equilibrium inside the device (e.g. non-compliant balloon), ensures that prior to application of substantial forces to any portion of the annulus, the entire device contacts the annulus.

(iii) Clear detection of tissue contact event—once the device fully contacts the tissue, additional expansion causes a rapid build up of pressure in the device (e.g. in the non-compliant balloon), providing the physician with simple alert that the balloon is 'firmly' contacting the tissue. In addition, design of the device ensures that contact with the leaflets can be differentiated from contact with the annulus.

(iv) Manipulation of tissue following contact—the physician can apply additional pressure to the tissue in a controlled manner thereby enabling specific clinical treatment, and preparation of the tissue opening for subsequent treatment.

(vi) Device can assume collapsed minimal footprint state following use—in the balloon-cage embodiment, deflation of the balloon leads to collapse of the cage and the diameter of the device is reduced back to its original pre-deployment diameter.

Thus, according to one aspect of the present invention there is provided a device for determining a physical parameter of a tissue opening, such as a valve annulus.

As used herein, the phrase "physical parameter" when utilized in context of a tissue opening such as a valve annulus, relates to a size, shape, elasticity and the like.

As used herein, the phrase "tissue opening" refers to an opening within a vessel, duct, valve or organ. Although the following description relates to a device configured for determination of a physical parameter related to a valve annulus, adapting such a device for use in, for example, sizing of a blood vessel lumen or a duct opening is well within the skill of the ordinary skilled artisan.

The device of the present invention includes an expandable member which is designed for positioning within a valve annulus. The device is configured for attachment to a catheter which can be used to guide the device within the body to the target annulus. Such a catheter is further described hereinbelow.

The expandable member is capable of expanding while applying an inward radial force (i.e. a force directed towards the central axis of the device).

As is further described hereinunder, such a force can be related to the diameter of the expandable member, and as such, when the expandable member is positioned within a valve annulus and expanded, an increase in the inward radial force induced by contact between the expandable member and tissue defining the annulus can be utilized to derive information relating to the physical parameter of the valve (e.g. size and/or shape).

Figure 1B:
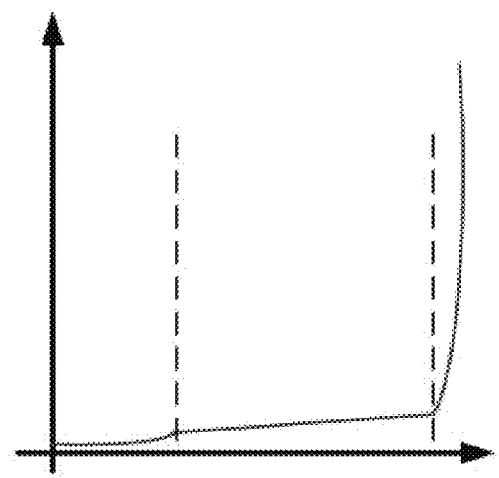
Figure 1C:
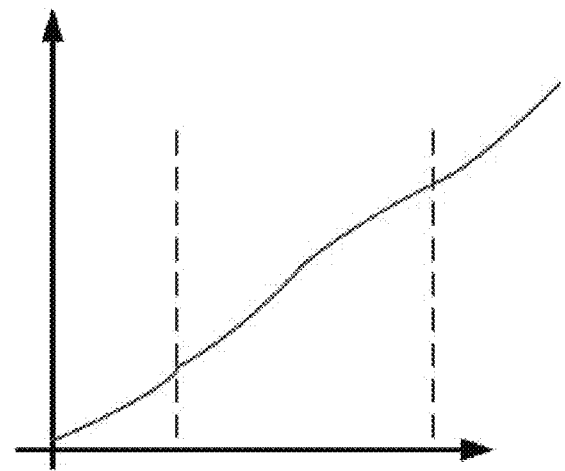

The expandable member of the present device traverses the limitations of prior art devices by providing a design which can be used to accurately define a point in expansion at which the expandable member contacts the tissue surrounding the opening. Such an indication cannot be accurately provided over a wide range of tissue opening sizes by either compliant or non-compliant balloons. FIGS. 1a-c illustrates the pressure-volume response curve of a non-compliant balloon (FIG. 1b), a compliant balloon (FIG. 1c) and the expandable member of the present device (FIG. 1a). These curves clearly illustrate that compliant and non-complaint balloons cannot be effectively used for sizing over a wide range of valve annulus sizes (e.g. 20-40 mm diameter). The inability of such balloons to provide accurate multi-sizing information explains why such balloons are used in sets of varying balloon sizes which are employed in a sequential best-fit approach.

Figure 2A:
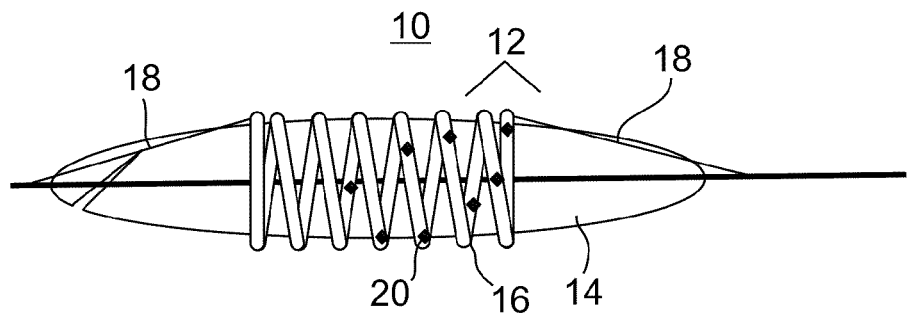
FIG. 2A illustrates one configuration of the present device which includes a wire cage encompassing a non-compliant balloon (dots represent optional imaging markers).

FIG. 2a illustrates one embodiment of the present device which is referred to herein as device 10.

Device 10 includes an expandable member 12 which is constructed from a non-compliant fluid filling reservoir 14 (e.g. balloon), fully or preferably partially encapsulated by a compliant structure 16 (e.g. formed as a cage, spiral, mesh or band/cuff). A cage configuration of structure 16 can be fabricated from a wire or fabricated (e.g. laser cut or etched) from a tubular structure. A band or cuff configuration of complaint structure 16 can be fabricated from elastic polymeric material (e.g. cut from a silicone tube or welded/glued from a silicone sheet). In any case, structure 16 can be fabricated from any material or shape which would provide the necessary elastic compliance.

Structure 16 is preferably attached to reservoir 14 via securing elements 18 which enable structure 16 to expand over reservoir 14 and yet maintain structure 16 attached to reservoir 14. Cage is anchored to balloon in both ends, so that expansion occurs when cage material extracts as well as shape changes. There is no cage—balloon relative movement. Anchoring methods are well known in prior art. For example, structure 16 and reservoir 14 can be. Alternatively, both reservoir 14 and structure 16 can be co-attached to catheter 102.

Reservoir 14 can be constructed as a balloon or sac using well known materials and approaches (e.g. by blow molding or extruding polyamide polymers) used in manufacturing of Percutaneous Transluminal Coronary Angioplasty (PTCA) balloons. Structure 16 can be fabricated from a polymer (e.g. silicone), a metal (e.g. titanium), an alloy (e.g. NITINOL) or any combinations thereof using approaches well known in the art. For example, via etching or laser cutting.

Reservoir 14 functions in applying an outward force to structure 16 thereby expanding it. In response to such an outward force, structure 16 expands and as a result of its elasticity applies an inward radial force.

For example, pressure for forcing leaflets towards annulus tissue is negligible (<4 atmospheres). When structure 14 contacts annulus tissue, the pressure within reservoir 14 rises to 6-8 atmospheres and therefore the inward elastic force of structure 16 (as translated to pressure within reservoir 14) should be less than 4 atmospheres, preferably less than 2 atmospheres. In such a case, contacting the leaflets would not produce a substantial change in pressure, whereas contacting the annulus tissue would result in a sharp change in pressure which can be detected.

For example, a non-compliant balloon functioning as a reservoir 14 will apply an expansion force to structure 16 as it is filled with a fluid such as saline. Such an expansion force will expand an elastic cage-shaped structure 16 encapsulating the balloon. Expansion of the cage will result in an elastic response and a generation of an inward force which is in a range of at least half, preferably at least a quarter to at least a tenth of the force applied by the tissue on structure 16 (at contact).

Inflation of reservoir 14 during expansion of expandable member 12, proceeds initially without buildup of pressure. As fluid is further delivered into reservoir 14 pressure builds up within reservoir 14 due to expansion of structure 16, from this point on, structure 16 will increase in diameter with an increase in pressure. Since the pressure is now uniform throughout reservoir 14, the pressure applied to a tissue by structure 16 or an uncovered portion of reservoir 14 (in the case of a reservoir no fully encapsulated by structure 16) will be the same. It should be noted that in the case of a partially encapsulated reservoir 14 (e.g. a case wherein reservoir 14 is not encapsulated at its end portions), reservoir will completely fill at such end portions prior to any buildup of pressure and further addition of fluid will then expand the middle (encapsulated) portion of reservoir 14 thus applying an outward pressure which will expand structure 16.

Throughout this entire process, the P over V slope will be relatively linear due to the compliant nature of structure 16. Once structure 16 fully contacts tissue surrounding the opening, further inflation of reservoir 14 is preformed against force applied by the tissue and thus pressure will rapidly rise within reservoir 14 providing an indication of full tissue contact and enabling extraction of corresponding volume of reservoir and diameter of expandable member 12.

Thus, reservoir 14 and structure 16 co-function to provide a compliant elastic structure which has an elastic expansion range of 20-40 mm, far greater and more linear than that of an elastic balloon. The relationship between these components of the expandable member of the present device is further described in the Examples section which follows.

Expandable member can also be fabricated from a unitary sac-like body which includes a compliant middle portion (annulus-contacting portion) and ends which are non-compliant. Such a unitary body can be fabricated by gluing non-compliant ends (closed) to a compliant tube section.

When inflated, such an expandable member first fills at the non-compliant ends (to form a dog bone shape), once the ends are filled, pressure builds up and further filling radially expands the compliant middle portion (which applied an inward radial force as it expands). Such a unitary body embodiment can also include embedded metal rods or spheres for additional elasticity (at the middle portion) and/or to provide imaging contrast.

An alternative configuration of the present device can include an elastic cage structure (such as that shown in FIG. 2a) which is expanded via tensioning of an axial wire (connected between the longitudinal ends of the cage). In such a configuration tensioning of the axial wire pulls the ends of the cage inward and expands the cross sectional diameter thereof. As the cage is expanded, its elastic response pulls on the wire ends and applies tension to the axial wire such that additional inward force applied to the cage by the tissue (at initial contact) increases the tension force on the axial wire and provides a point of detection.

A similar configuration having a cage that assumes a fully expanded structure when not tensioned can also be used. In such a configuration, the cage is fully expanded when no tension is applied to the axial wire, tensioning of the wire collapses the cage to its compacted (delivery) state. Expansion of the cage is effected by slowly releasing the tension on the axial wire and point of tissue contact is detected by a drop in wire tension.

Thus, the expandable member forms a semi-compliant structure that provides a user of the present device with force feedback information that can be used to determine initial contact between the expandable member and tissue surrounding an annulus. Such feedback can be provided over a wide range of expansion sizes (20-40 mm) thus providing the present device with multi-sizing functionality. Feedback can be provided to the user through volume and/or pressure measurements. For example, inflation may be stopped by the user (or automatically via a controller) once P or V or dP/dV gets to a predefined value. Since the user or system controls flow rate into and out of the balloon, inflation and deflation are controlled and the procedure can be accurately timed. Inflation/deflation can be calibrated per balloon size. The system can identify the balloon size used (e.g. 14-20, 18-24 or 22-28 mm) and adjust inflation/deflation time accordingly or provide the user with the inflation/deflation times.

Since the device of the present invention is used by the physician prior to prosthetic valve placement, the present device can also be used to mark the valve (e.g. valve annulus) with a contrast agent and thus facilitate accurate guiding and positioning of the prosthetic valve. Examples of contrast agents include water soluble or water insoluble radiopaque contrast agents. Examples of water soluble radiopaque contrast agents include metrizamide, iopamidol, iothalamate sodium, iodomide sodium, and meglumine. Examples of water insoluble radiopaque contrast agents include metals and metal oxides dyes or microsphere suspensions, gels and the like.

Such contrast agents can be delivered into annulus or leaflet tissue via a cannula or needle mounted on a catheter carrying the present device. The catheter or device can also include a reservoir filled with the contrast agent. Since the device of the present invention can be accurately positioned within the valve and anchored therein (further described hereinbelow), it can also serve to accurately guide a delivery cannula or needle to the annulus or leaflet tissue.

The present device can also be utilized for determining a shape of a tissue opening such as a valve annulus.

One preferred approach for such shape determination is described in Example 2 of the Examples section which follows. This approach utilizes a plurality of imaging markers (e.g. radio-opaque, fluorescent, RF, or ultrasound markers) arranged in a pattern on the expandable member. When the expandable member is positioned in the tissue opening and expanded, positioning of these markers with respect to each other can be used to determine a cross sectional shape of the expandable member and thus a cross sectional shape of the tissue surrounding the opening.

Shape extraction also enables determination of a projection plane which is most perpendicular to the device and thus most perpendicular to the annulus. Information relating to the projection plane of the annulus can be used by a physician to subsequently deliver and accurately position a prosthetic valve.

In order to enable such functionality, the marker pattern disposed on the expandable member of the present device is designed according to the considerations provided in Example 2 of the examples section which follows.

For example, gold markers can be mechanically applied to structure 16 (via crimping) or glued or heat-fused thereto (point welding). Alternatively, a Barium Sulfate or Tungsten Carbide solution can be mixed into a polymer material prior to fabrication of the present device.

To enable accurate positioning within a specific zone of a tissue opening, the present device can also include a tissue engagement mechanism which ensures that the expandable member is correctly positioned within the desired zone of a tissue opening. This feature is particularly useful on cases where the tissue opening is defined by a narrow tissue zone (e.g. valve annulus) since in such cases, positioning of the expandable member within the desired zone in the tissue opening and/or maintaining such positioning throughout a procedure can be difficult to achieve.

One proposed gripping structure can be constructed by covering only a middle portion of reservoir 14 with structure 16. In such a configuration, inflation of reservoir 14 will initially cause expansion of the non-compliant uncovered end portions of reservoir 14. When expandable member is located within an annulus, the inflated end portions can be used to immovably locate the middle (and covered) portion of expandable member 12 within the annulus.

The device of the present invention can also incorporate elements that can be used to score (notch) valve leaflet tissue. This feature is particularly useful in heart valve stenosis, where fibrosis of the valve leaflets may limit the opening size of the heart valve.

The scoring process is based on Stress Concentration principle wherein a very narrow point or edge applies force over a surface, local contact forces will rise dramatically as function of the "in contact" surface area.

One embodiment of a scoring configuration can be effected by constructing structure 16 from very thin wires (or struts) and then shaping them with a very narrow edge on an external side (facing the tissue). Such wires or struts would score or notch calcified leaflet tissue with application of minimal pressure. An alternative configuration can include very thin wires over-molded onto the outer surface of a compliant silicone tube (forming structure 16). Once this tube expands, the wires will extend out and form as sharp edges to enable scoring.

The present device is preferably mounted on a catheter which forms a part of a system which facilitates positioning of the present device as well as providing expansion and detection functionalities.

Thus, according to another aspect of the present invention there is provided a system for determining a physical parameter of a tissue opening.

Figure 2B:
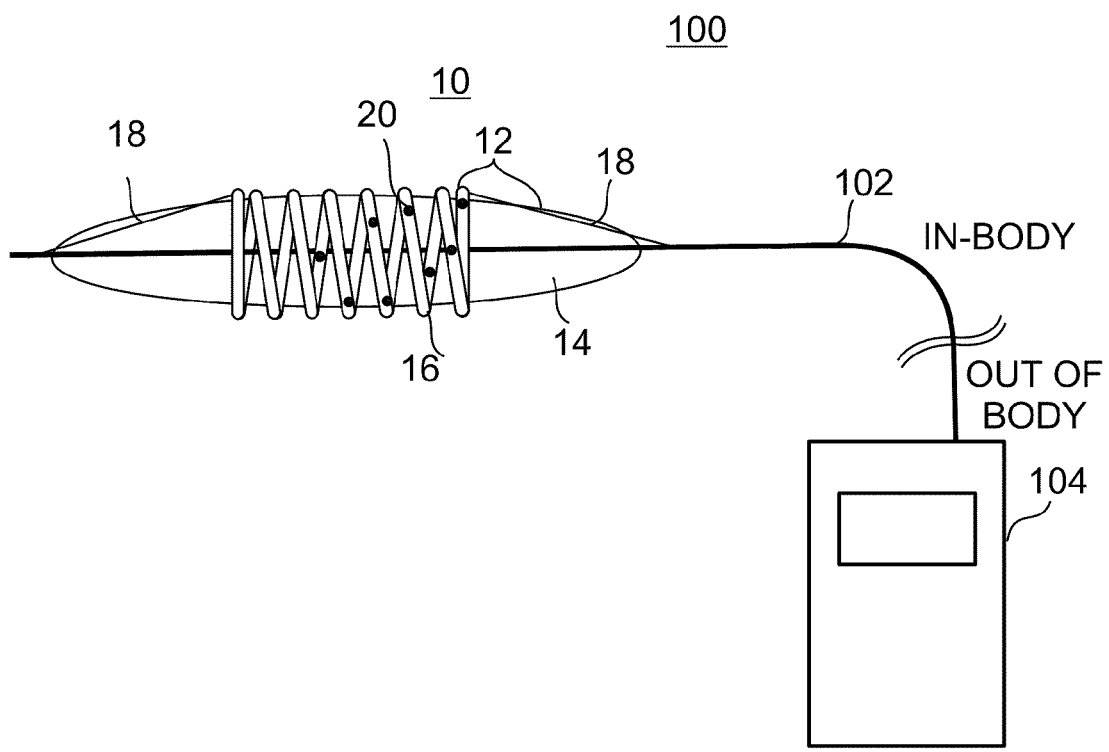
FIG. 2B illustrates a system for determining a physical parameter of a tissue opening constructed in accordance with the teachings of the present invention.

FIG. 2b illustrates the present system which is referred to herein as system 100.

System 100 includes device 10 which is fitted on, or integrated with a catheter 102. Catheter 102 can be any percutaneous delivery catheter, preferably, catheter 102 is an over-the-wire Valvuloplasty (or other) catheter with enhanced strength pushability, and a flexible distal tip. Reservoir 14 can be directly attached to, or formed with catheter 102. In such a configuration, reservoir 14 is preferably a non-compliant polyamide balloon capable of expanding to a diameter of 35-40 mm and holding a pressure of up to 8 atmospheres. The balloon can also include radio-opaque marker rings at both ends and at mid length.

System 100 further includes a control unit 104 which is connected to an extracorporeal end of catheter 102. Control unit 102 includes a Fluid Pressure Sensor (with a range of 1-15 atmospheres), a flow meter capable of measuring a volume of fluid inserted into the catheter system, a manual or automatically controlled pump with a 1-15 atmospheres range and a standard catheter interface (as is utilized in the art). Control unit 102 further includes a processing unit which executes algorithms suitable for processing pressure and flow data and perform real-time tracking over measured pressure and volume, detect changes in the pressure/volume ratio and provide a user with audio and/or visual feedback.

System 100 can be used for sizing and shape determination of a valve annulus as follows.

A guidewire is inserted into a heart chamber and catheter 102 is positioned over the wire to a desired location. Once catheter 102 and mounted device 10 are positioned an imaging C-arm is maneuvered over the site of imaging and used to ascertain that device 10 of system 100 is positioned in place, by imaging and identifying markers 20 and the annulus tissue.

Reservoir 14 of expandable member 12 is inflated via transfer of saline from the pump of control unit 104. Initial inflation of the two non-complaint regions flanking the compliant central region creates a dog bone shape which flanks the annulus and thus secures expandable member 12 in position. Once inflation has expanded expandable member 14 to a point where it contacts annulus tissue, control unit 104 informs the physician of full contact via a displayed or audible message; control unit 104 can display a calculated diameter of the annulus to the physician.

The physician then images the annulus at a first projection angle. Once markers 20 are identified, control unit 104 will direct the physician to capture one or more additional images at a specific projection angle (of the C-arm camera) or a range of projection angles. Once imaging is complete, reservoir will be deflated; control unit of system 100 will automatically select the best image or images, identify markers 20 in the image(s) and determine the 2D position of each marker 20.

Control unit 104 will then compute a cross section of expandable member 12 (as is further described in the Examples section which follows) and display a shape and size of the annulus to the physician.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Valve Size Determination Using a Non-Compliant Balloon Encapsulated by a Nitinol 'Cage'

One configuration of the present device can be constructed by encapsulating a central portion of a non-compliant balloon (EXAMPLE) with a Nitinol 'cage'-like structure (see, FIG. 2a). The ends of the cage are attached to the distal and proximal ends of the balloon to secure the cage to the balloon and prevent slippage. Inflation of the balloon forces near-linear elastic expansion of the cage which enables prediction of cage size according to volume of fluid in the balloon.

Figure 3A:
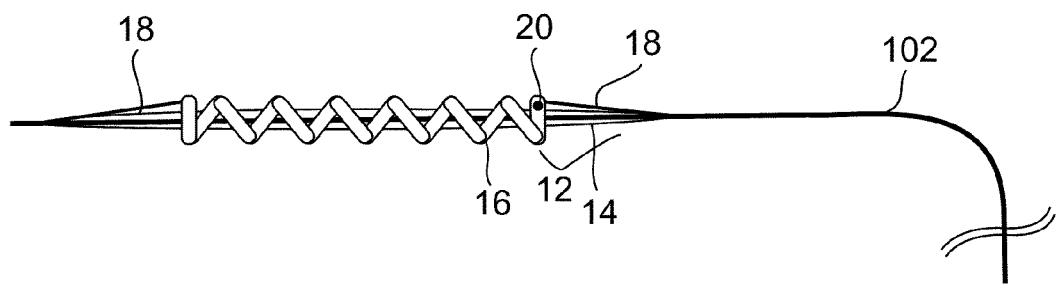
FIGS. 3A-B illustrate expansion of the device of FIG. 2 via fluid delivery to the non-compliant balloon.
Figure 3B:
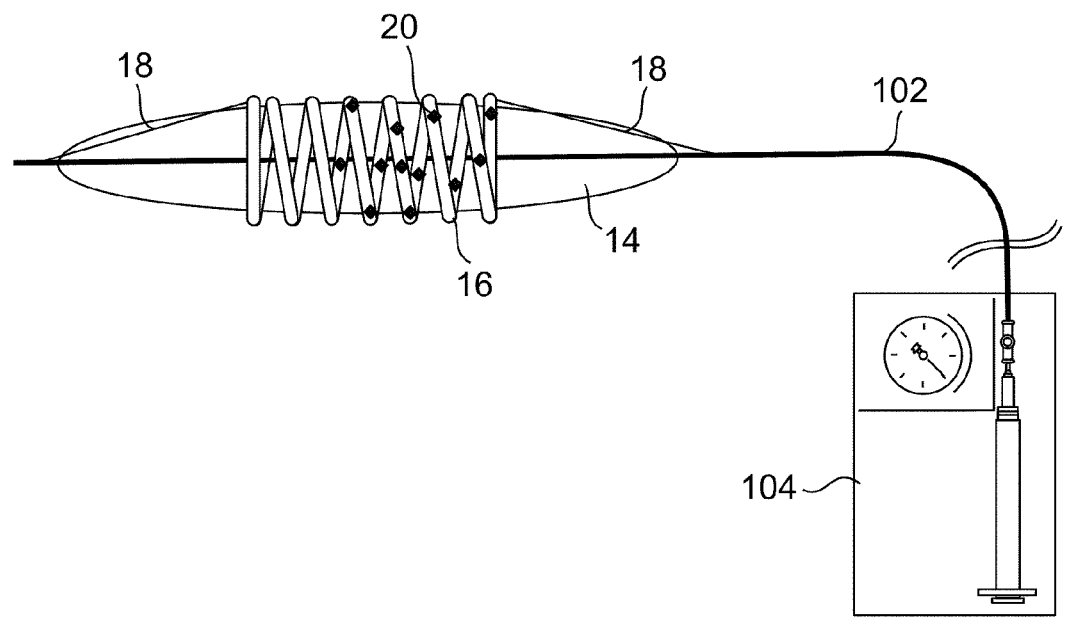

The cage is designed to have a "free shape" for example, a collapsed spring, with a minimum diameter (MD) and an elastic diameter (ED) range (a range of diameters throughout which the cage remains elastic). It is further designed to generate a radial collapsing force (toward the center of the balloon) throughout expansion (FIGS. 3a-b).

Expansion of the balloon via delivery of fluid thereto causes a pressure build up due to the radial inward force of the cage. The larger the cage diameter, the larger the pressure of the fluid within the balloon.

The relationship between the volume of the balloon and radial inward pressure of the cage can be represented by equation 1:

$$P = f(V) - P_0$$

Where:

V—is the volume of the fluid injected into the balloon $f$—is a function of V. The cage is designed with an f as close as possible to a constant factor $P_0$—is the offset pressure (only in case the cage has an ED which is larger than the MD; where ED=MD, $P_0$=0).

Figure 4A:
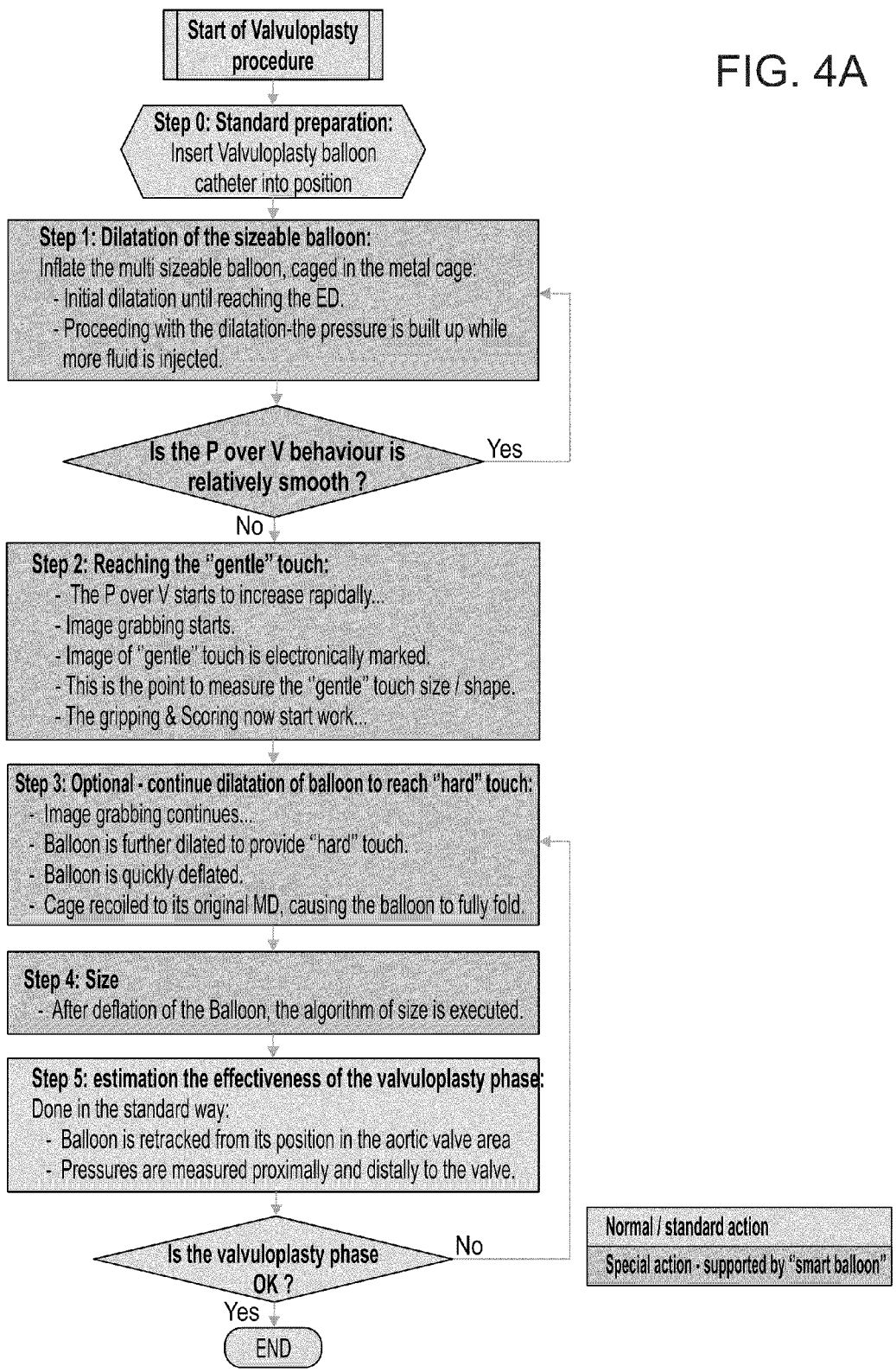
FIG. 4A is a flow chart diagram illustrating size determination using the device of FIG. 2.
Figure 4B:
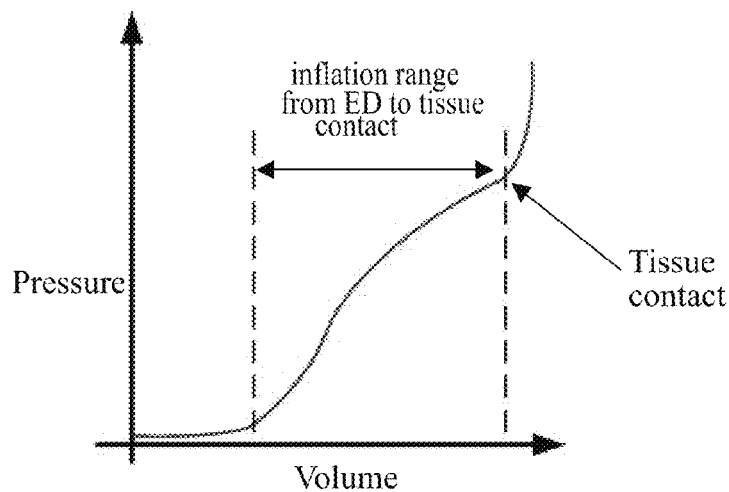
FIG. 4B is a graph of Volume Vs. Pressure which can be used to determine valve annulus size using the device of FIG. 2, double headed arrow shows the elastic response of the device from the point of an initial elastic diameter to a diameter achieved at tissue contact (noted by single headed arrow).

FIG. 4b graphically illustrates pressure buildup inside the balloon versus the volume of the balloon and cage.

Since the present device includes a compliant member (an elastic cage, or an elastic cuff/band) and a non-compliant member (the balloon), elastic expansion thereof can be effected throughout a wide range of expansion diameters (partial range shown by double headed arrow); the expansion range of the non-compliant balloon is only limited by its final expanded size, while the elasticity range (the ED range) is a function of the cage.

Thus, this unique combination of features provides a multi-sizing device which can be used to accurately size a wide range of valves using a single device.

Delivery and use of the present device is illustrated by the flow chart of FIG. 4a. The device of the present invention forms a part of a system (FIG. 2b) which is utilized to deliver the present device into the body in a manner similar to delivery of a valvuloplasty balloon. The device is then positioned within the annulus zone of the valve and is expanded via delivery of fluid (e.g. saline) from a dilatation pump.

Prior to contact between the cage and valve tissue surrounding the annulus, pressure build up in the balloon is a function of equation 1.

When the cage initially contacts the valve tissue (e.g. leaflets of a cardiac valve) an additional force (supplementing the radial collapsing force of the cage) is applied to the cage. This additional force translates into a pressure increase within the balloon with further volume increases.

This additional force can be detected as a deflection point in a graph of pressure Vs. volume (single headed arrow, FIG. 4b). This deflection point represents first contact between the cage and valve tissue.

Identification of this contact point can be effected by providing the physician with a pressure readout mechanism that clearly and simply indicates non-linear pressure buildup. Such a mechanism can be a simple pressure gauge or a graphical display indicating pressure buildup changes.

The pump monitors the volume of fluid that is injected into the balloon, while measuring the pressures that develops, therefore, a graph of P over V can be extracted from pump parameters.

Currently, the following relations can be derived from monitoring the V and P:

1 P (the pressure) Provides an estimation of the cage diameter, sufficiently accurate even in cases where the annulus is an ellipse.

2 V (volume of fluid) can be used to estimate cage diameter, a combination of P and V provides an accurate estimation of the effective diameter of the cage and balloon.

3 dP/dV Provides the "slope" of a P vs. V graph. As long as the device has not contacted the tissue, the slope is relatively moderate. Once the tissue surrounding the annulus applies a force to the cage, the pressure builds up rapidly and the slope of the graph becomes steeper. Thus, monitoring of dP/dV can provide the point of tissue contact and an accurate assessment of size.

Since P is already monitored by the pump a dP/dV measurement can be effected externally without interrupting the regular path of the fluid: just by introducing small volume fluctuations into the balloon, and monitoring the pressure changes correlated to these volume fluctuations. In such an implementation, the physician can be automatically alerted by a monitoring system and provided with an indication of tissue contact.

Example 2

Valve Shape Determination using a Non-Compliant Balloon Encapsulated by a Nitinol 'Cage'

The device described in Example 1 can be provided with markers (e.g. radio-opaque, ultrasound, fluorescent or RF markers) and used to determine valve annulus shape.

Basically, once contact between the cage and tissue surrounding the annulus is determined (as described above), the markers disposed on the cage can be used to determine the shape of the annulus.

During a procedure the present device is introduced in the body of a subject and the region of expandable member carrying the markers is positioned within the valve annulus (which can be identified via imaged calcification). The expandable member is deployed (e.g. the non-compliant balloon is inflated); once the expandable member contacts the annulus tissue, the physician images the annulus from two or more imaging angles. The imaging angles can be determined by the present system according to the pattern and position of the markers on the expandable member.

Once imaging is complete, the expandable member will be collapsed and the device removed from the body.

For each imaging angle the present system will select a best image, identify markers on the image and segment (x, y position) the markers. As is further described below, the imaged markers can then be uniquely identified and used to determine the cross sectional shape of the expandable member and as a result the shape of the annulus.

Mathematical Solution for Shape Reconstruction

In the embodiment of the device presented in Example 1, an outer cage fitted on a balloon can be marked with markers A to E (using 4-8 identifiable markers is preferred).

At least some of these markers will need to have a uniquely identifiable signature (e.g. shape, size, type of imaging signal).

Figure 5A:
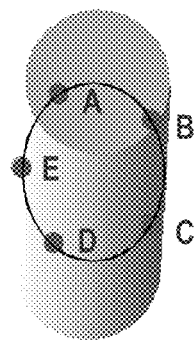
FIGS. 5A-F illustrates use of marker patterns for the purpose of shape determination in a device constructed in accordance with the teachings of the present invention.
Figure 5B:
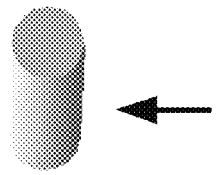
Figure 5C:
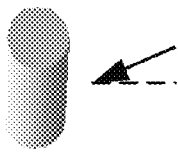

FIG. 5a illustrates such markers disposed around the periphery of the expandable member. For simplicity, the expandable member is represented by a cylinder. Imaging of these markers from a first imaging angle (for example—the current delivery projection, usually perpendicular to the expandable device) results in the image depicted in FIG. 5b. Imaging of the same markers from a second imaging angle (at an angle of, for example, 30° from the first imaging plane) results in the pattern shown in FIG. 5c.

One can employ forward ray intersection and ellipse adjustment to reconstruct these imaged markers into a shape. Non-linear optimization through iterative least squares minimization will yield the most accurate results and the most accurate error propagation.

In other words, since the 2D position of a specific marker on two images, and the imaging geometry (projection angles, Source to Image distance, etc.) are known, one can use compute the 3D position of each specific marker by intersecting the two vectors defined by the position of the marker in the two 2D images. Due to noise, inaccuracy of data, errors in identification and the like, such vectors will not intersect. To correct for such noise and errors, an iterative process running gradually changing input parameters (markers 2D position and/or C-ARM geometry) can be used to identify intersections and eventually solve the 3D position (x,y,z) of each marker. Once these points are derived, shape (as well as size) can be extracted.

Numerous approaches can be used to construct a shape from the imaged markers. For example, forward ray intersection is detailed in Three-dimensional reconstruction of curves from pairs of projection views in the presence of error. I. Algorithms, Med. Phys. Volume 24, Issue 11, pp. 1671-1678 (November 1997). Least Square optimization is detailed in Observations and Least Squares, By Edward M. Mikhail, Friedrich E. Ackermann, Published by IEP, 1976, ISBN 0700224815, 9780700224814.

Coding of Markers

Coding of markers is required to facilitate a unique identification of a marker on two images. It is possible to uniquely code only the markers which serve as anchors for unique identification of all markers.

Coding is dependent on the material of the expandable member and the marker material.

Figure 5D:
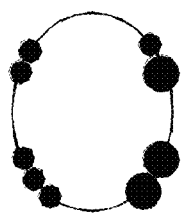
Figure 5E:
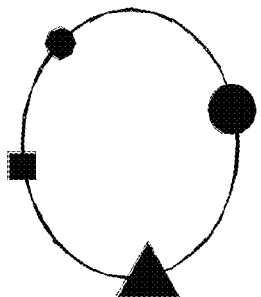

Several coding possibilities can be used with the expandable member of the present device. For example, FIG. 5d illustrates pattern coding in which marker pairs or triplets or markers of varying sizes generate a uniquely perceptible marker pattern. FIG. 5e illustrates a coding pattern which is shape dependent. A combination of these two types of coding approaches can also be used.

Figure 5F:
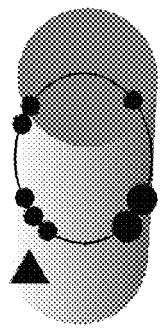

FIG. 5f illustrates an expandable member having 4 uniquely identifiable markers as well as an aiding marker which is separated from the markers used for shape identification. Such aiding markers can be used in 'pointing' to a specific marker (like the triangle "pointing" to the triplet marker).

The markers are preferably disposed on a plane which is slightly offset from a plane perpendicular to the longitudinal axis of the expandable member. Such a slight tilt enhances imaging visibility of markers, especially in the perpendicular imaging plane, since such an imaging plane can result in a straight line of markers (see FIG. 5b).

Alternative Marker Approaches

Figure 6:
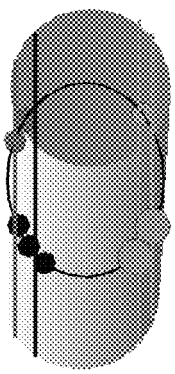
FIG. 6 is a marker embodiment of the present device which employs line-markers. Each marker is set along a specific line running the length of the outer surface of the expandable member. Once a marker is uniquely identified, the entire line can be uniquely identified.

The cage of the expandable member can be marked with imaging lines along its longitudinal axis (FIG. 6). Each marker is set along a specific line, once a marker is uniquely identified, the entire line can be uniquely identified and associated with the specific marker.

Example 3

Using a Semi-Compliant Balloon to Measure Valve Annulus Diameter

Volume and pressure were measured during inflation of a semi-compliant balloon in order to illustrate that dP/dV can be used to determine the average diameter of valve annulus and in order to assess an optimal pressure range that can be applied to a valve annulus.

Figure 7:
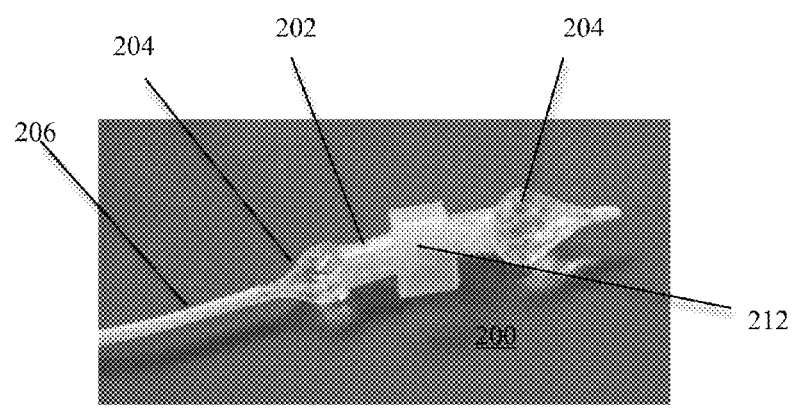
FIG. 7 illustrates a semi-compliant balloon used for testing a relationship between annulus diameter measurements and dP/dV.
Figure 8:
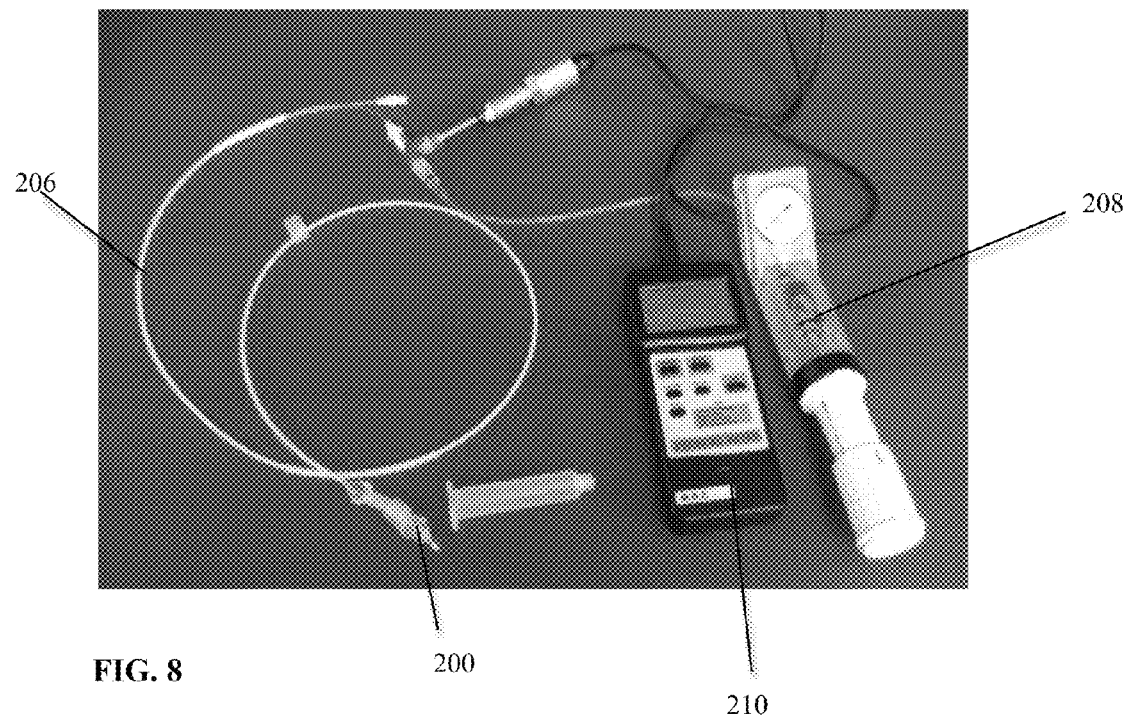
FIG. 8 illustrates a system used along with the balloon of FIG. 7.

A semi-compliant balloon 200 constructed from a compliant silicone tube midsection 202 and non-compliant balloon (TYSHAK balloon available from NuMed) ends 204 (FIG. 7) was connected via a balloon catheter 206 to a volume calibrated pump 208 (FIG. 8). A digital pressure gauge 210 was connected in line between the pump and balloon (FIG. 8) and was used to record pressure readings from the balloon. Cuffs 212 (FIG. 7) of varying diameters were each separately used to simulate a valve annulus by fitting each over midsection 202 of balloon 200 prior to inflation.

Figure 9A:
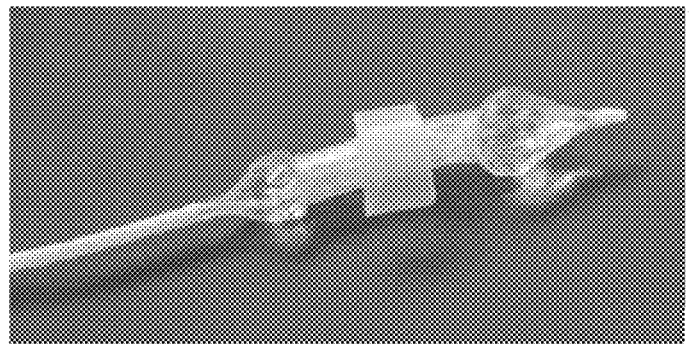
FIGS. 9A-C illustrate an inflation sequence of the device of FIG. 7 positioned within a cuff simulating a valve annulus.
Figure 9B:
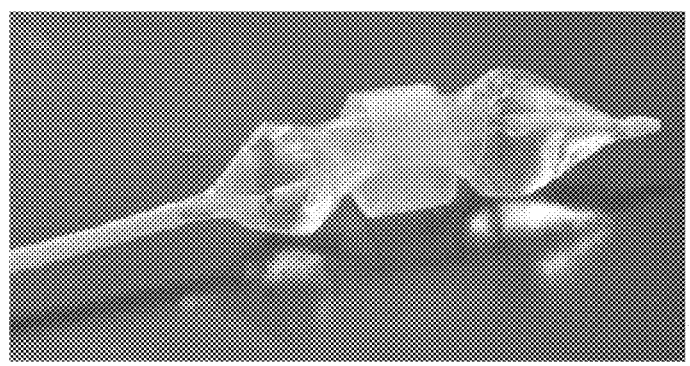
Figure 9C:
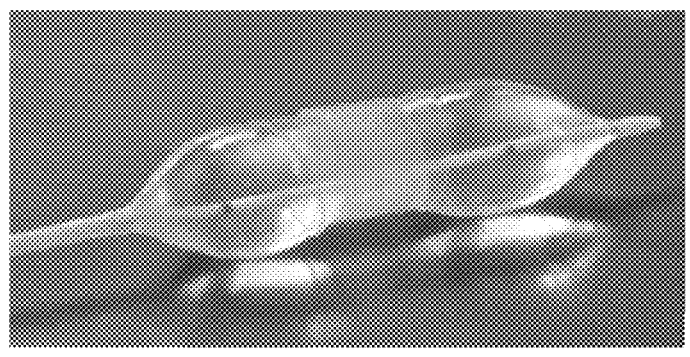
Figure 10:
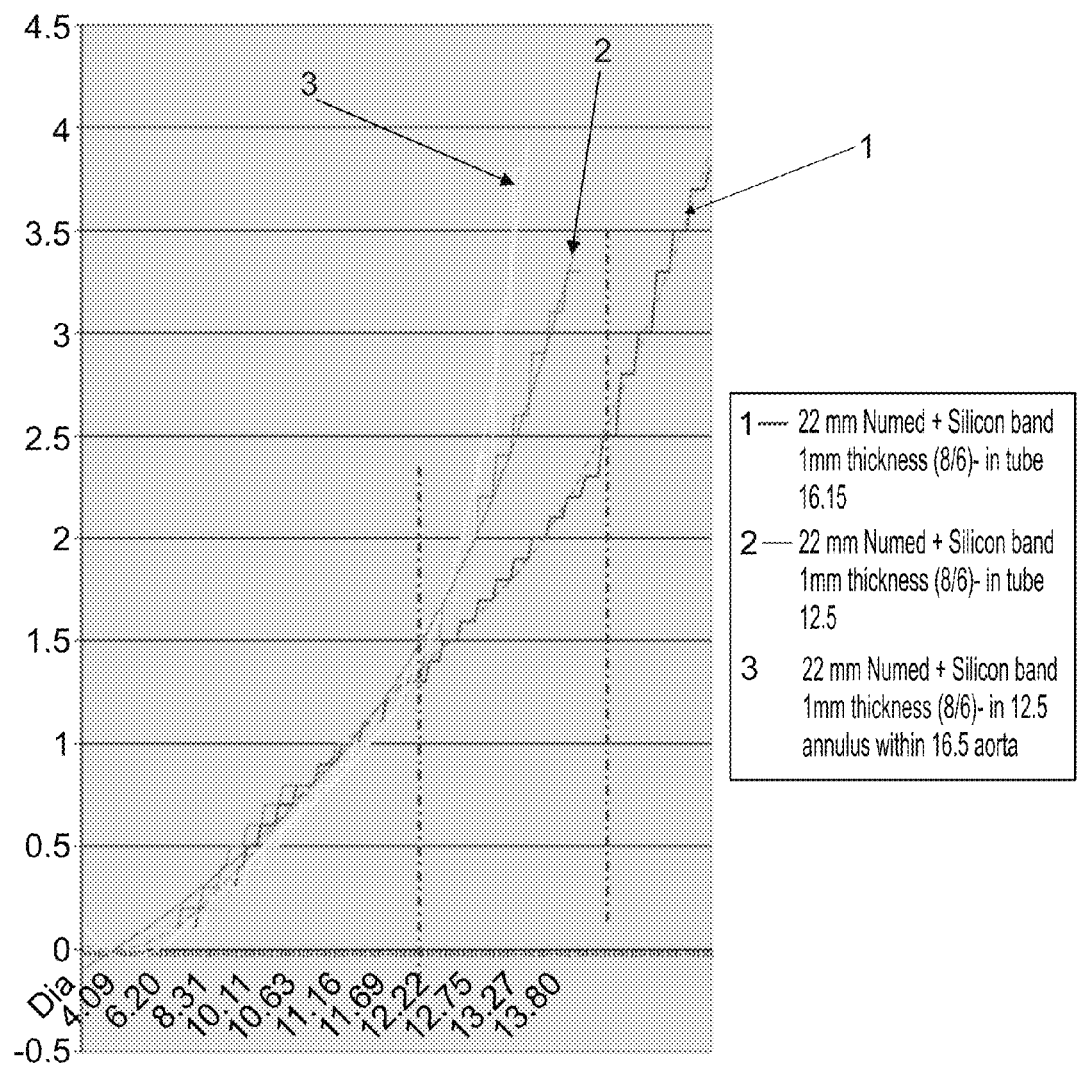
FIG. 10 is a graph illustrating the pressure/volume measurements from a balloon inflated within 2 different cuffs. The smaller cuff is 12.5 mm in diameter and represents the diameter of an opening of a stenotic valve; the larger cuff is 16.5 mm in diameter and represents the annulus diameter.

FIGS. 9a-c illustrate the sequence of inflation of balloon 200 disposed within cuff 212. At each point of inflation, pressure was measured using digital pressure gauge 210 and correlated to the volume of fluid in balloon 200. The resultant pressure/volume curve of balloon 200 inflated within 2 different cuffs 212 (with diameters of 12.5 and 16.5 mm) is shown in FIG. 10. FIG. 10 also illustrates a third graph, where the balloon is inserted into 2 different cuffs. The smaller cuff is 12.5 mm in diameter and represents the opening diameter of a stenotic valve; the larger cuff is 16.5 mm in diameter and represents the annulus diameter.

FIGS. 11a-b illustrate side by side the pressure/volume (FIG. 11a, which is identical to FIG. 10) and dP/dV (FIG. 11b) measurements from balloon 200. One can see, that due to the compliant member added to the balloon, the P/V slope has a specific shape. When the balloon reaches the size of the cuff, the P/V slope steepens, due to pressure (P) buildup and only a negligible change in volume (V). This slope represents the derivative of P according to V (dP/dV). The region in this graph where dP/dV gets much steeper represents the point where the balloon contacts the cuff and simulates contact between the present device and the valve annulus.

Based on the above description and analysis one can determine the pressure and volume point in inflation at which the device contact resistant tissue (e.g. stenotic valve leaflets or valve annulus). Since the volume of the balloon can be determined at any point during inflation and during tissue contact, one can use the present system to, for example, measure the diameter of the annulus.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for determining a physical parameter of a tissue opening comprising a catheter having a semi-compliant expandable member including a non-compliant inflatable balloon at least partially covered by an elastic cage configured having a wire mesh, a wire spiral or wire struts, said elastic cage anchored to distal and proximal ends of said balloon, said expandable member being capable of expanding while applying an inward radial force indicative of a diameter thereof, such that when said expandable member is positioned within a tissue opening and expanded, an increase in said inward radial force can be indicative of contact between said expandable member and tissue surrounding the tissue opening.

2. The device of claim 1, wherein said increase in said inward radial force can be utilized to derive information relating to the physical parameter of the tissue opening.

3. The device of claim 1, wherein the tissue opening is a valve annulus.

4. The device of claim 1, wherein said expandable member has an elastic diameter range of 4-35 mm.

5. The device of claim 1, wherein said physical parameter is a diameter of the tissue opening.

6. The device of claim 1, further comprising a plurality of imaging markers attached to said expandable member.

7. The device of claim 6, wherein said plurality of imaging markers are arranged in a pattern selected for indicating a cross sectional shape of said expandable member when in an expanded state.

8. The device of claim 1, wherein said cage is capable of elastic expansion without substantial structural deformation when expanded beyond a tissue contact diameter within the tissue opening.

9. A method of sizing a tissue opening comprising (a) inflating a semi-compliant expandable member disposed on a catheter within said tissue opening, said expandable member including a non-compliant balloon positioned within an elastic cage anchored to distal and proximal ends of said inflatable balloon; (b) measuring volume and pressure of said inflatable structure during said inflation; and (c) utilizing said volume and pressure measurements to determine a point of contact between said expandable member and tissue of the tissue opening to thereby size the tissue opening.

10. The method of claim 9, wherein the tissue opening is a valve annulus.

\* \* \* \* \*